United States Patent [19]

Butler

[11] Patent Number: 4,579,989

[45] Date of Patent: Apr. 1, 1986

[54] CONVERSION OF OLEFINS TO HIGHER MOLECULAR WEIGHT HYDROCARBONS WITH SILICALITE CATALYST

[75] Inventor: James R. Butler, Big Spring, Tex.

[73] Assignee: Cosden Technology, Inc., Dallas, Tex.

[21] Appl. No.: 496,380

[22] Filed: May 20, 1983

[51] Int. Cl.$^4$ ............................................. C07C 2/00
[52] U.S. Cl. .................... 585/415; 585/530; 585/469
[58] Field of Search ............ 585/407, 415, 530, 469, 585/646; 252/455 Z

[56] References Cited

U.S. PATENT DOCUMENTS

| | | | |
|---|---|---|---|
| 4,177,202 | 12/1979 | Chang et al. | 518/714 |
| 4,265,735 | 5/1981 | Audeh et al. | 585/408 |
| 4,270,017 | 5/1981 | Young | 585/437 |
| 4,320,241 | 3/1982 | Frankiewicz | 585/469 |
| 4,347,394 | 8/1982 | Detz et al. | 585/419 |
| 4,365,104 | 12/1982 | Kaeding | 585/467 |
| 4,387,260 | 6/1983 | Watson et al. | 585/467 |
| 4,394,251 | 7/1983 | Miller | 585/533 |
| 4,403,044 | 9/1983 | Post et al. | 585/408 |
| 4,414,423 | 11/1983 | Miller | 585/517 |
| 4,417,086 | 11/1983 | Miller | 585/530 |
| 4,417,087 | 11/1983 | Miller | 585/530 |
| 4,417,088 | 11/1983 | Miller | 585/533 |
| 4,423,268 | 12/1983 | Miller | 585/533 |
| 4,423,269 | 12/1983 | Miller | 585/533 |

FOREIGN PATENT DOCUMENTS 0035807 9/1981 European Pat. Off. ............ 585/714

OTHER PUBLICATIONS

Rao et al., Hydrocarbon Processing, Nov. 1980, pp. 135-142.
Rao et al., ACS Div. Fuel Chem. Prep. 25(2), 119-126, (1979).
Olson et al., J. Catalysis, 61, 390-396, (1980).

*Primary Examiner*—John Doll
*Assistant Examiner*—A. Pal
*Attorney, Agent, or Firm*—John K. Abokhair

[57] ABSTRACT

A process for converting a gaseous feed material including an olefinic mixture comprising primarily ethylene and propylene to higher molecular weight hydrocarbons such as gasoline range products including aromatics. The process comprises passing the feed material under conversion conditions through a reaction zone containing an unmodified crystalline silica polymorph silicalite catalyst. The feed material also contains catalytic poisons such as water, oxides of carbon or sulfur-containing compounds which are commonly encountered in refinery off-gas streams such as those coming from a fluidized catalytic cracking unit.

8 Claims, No Drawings

CONVERSION OF OLEFINS TO HIGHER MOLECULAR WEIGHT HYDROCARBONS WITH SILICALITE CATALYST

BACKGROUND OF THE INVENTION

The present invention relates to a process for converting a gaseous feed material including an olefin mixture containing catalytic poisons such as water, oxides of carbon or sulfur-containing compounds, into higher molecular weight hydrocarbons including gasoline range products having aromatics present therein.

The conversion of olefins to aromatic compounds is not new in the art. In U.S. Pat. No. 4,238,318 by Kouwenhouven et al, $C_2$–$C_5$ olefins or mixtures thereof were contacted with $C_1$–$C_5$ paraffins at elevated temperatures with an aluminosilicate catalyst to produce an olefinic gasoline range mixture containing less than 20% by weight of aromatics. A two step process was utilized wherein the lower olefins were first oligomerized to olefins with a higher molecular weight and thereafter the higher olefins were then passed over the aluminosilica catalyst to yield the gasoline range compounds containing aromatics. In the first step of the process considerably milder conditions were applied than in the second aromaticizing step.

In U.S. Pat. No. 3,756,942 by Cattanach, a liquid feed material consisting essentially of paraffins, olefins, naphthenes, and mixtures thereof having a boiling point in the range from $C_5$ and higher were converted to aromatics in the presence of a crystalline aluminosilicate catalyst of the ZSM-5 type.

In U.S. Pat. No. 3,760,024 by Cattanach, a feed consisting essentially of $C_2$–$C_4$ paraffins and/or olefins was converted to aromatics in the presence of a crystalline aluminosilicate catalyst of the ZSM-5 type.

In a typical refinery operation, a significant amount of ethylene and propylene is utilized as fuel gas for refinery boiler operations. For example, the untreated off-gas from a fluidized catalytic cracker typically used as boiler feed is high in both ethylene and propylene along with contaminants such as oxides of carbon and hydrogen sulfide. In addition, the off-gas usually contains a significant amount of water up to the saturation point of the off-gas. It can be appreciated that these refinery streams would be much more valuable if converted to gasoline products than if used as boiler feed. Previously described processes provide methods to convert olefinic streams into useful aromatic products however, these processes utilize catalysts which undergo substantial degradation when exposed to water, oxides of carbon or sulfur-containing components. In particular, aluminosilicate catalysts of the ZSM-5 series have been reported to be unsuitable in the presence of water in that they rapidly lose activity when steam or water is present during the reaction. What is needed therefore is a process for converting these contaminated off-gas refinery streams containing ethylene and propylene into higher molecular weight hydrocarbons including useful gasoline range end products. What is also needed is a process utilizing a catalyst which is not deleteriously affected by the presence of these contaminants.

Recently, catalysts characterized as crystalline silica polymorphs prepared in accordance with specified procedures and known generically as silicalite type catalysts, have been discovered to be useful in these olefinic conversion processes. These catalysts are not subject to deactivation in the presence of water, oxides of carbon or sulfur-containing compounds.

SUMMARY OF THE INVENTION

Therefore in accordance with the present invention there is provided a process for converting a feed material including an olefinic mixture containing catalytic poisons therein such as water, oxides of carbon, or sulfur-containing compounds into higher molecular weight hydrocarbons. The process includes passing the feed material under conversion conditions through a reaction zone containing an unmodified crystalline silica polymorph silicalite catalyst. The majority of the olefinic mixture includes ethylene and propylene such as would be found in the off-gas stream from a refinery fluidized catalytic cracking unit. The oxides of carbon most commonly found are carbon monoxide and carbon dioxide; the sulfur-containing compound most often found is hydrogen sulfide. The amount of hydrogen sulfide present commonly is less than 20% by mole of the total olefinic mixture whereas the amount of oxides of carbon present commonly are less than 5% by mole of the total olefinic mixture. In addition, the refinery off-gas stream contains an amount of water up to the saturation point of the off-gas stream. The conversion conditions include temperatures in the range of about 350° C. and about 650° C., pressures in the range of about 30 psig to about 300 psig, and a weight hourly space velocity across the catalyst from about 5 to about 50 based upon the weight of total feed per weight of catalyst per hour.

DETAILED DESCRIPTION OF THE INVENTION

The present invention comprises a process for converting a feed material comprising an olefinic mixture containing catalytic poisons into higher molecular weight hydrocarbons including gasoline range hydrocarbons. The process involves passing the feed material under olefinic conversion conditions through a reaction zone containing an unmodified crystalline silica polymorph silicalite catalyst therein.

Gasoline range hydrocarbons are defined as those aliphatic and aromatic hydrocarbons from about $C_5$ to about $C_{12}$, but they do not include those non-hydrocarbon additives commonly added to gasoline. Certain $C_4$ streams such as isobutene may also be included in gasoline range products.

Catalytic poisons, as defined in G. Hawley *Condensed Chemical Dictionary* incorporated herein by reference, are those compounds known to reduce or destroy the activity of a catalyst, and in particular those compounds having deleterious effects on many aluminosilicates such as the zeolites. A principal feature of the present invention is the use of a catalyst to convert olefinic streams to higher molecular weight hydrocarbons in the presence of those catalytic poisons such as water, oxides of carbon or sulfur-containing compounds. Historically, water has been a poison to aluminosilicate catalysts requiring its removal from feedstreams prior to passage over the aluminosilicate catalysts. It is generally believed that the activity of these catalysts is proportional to the aluminum concentration and that steam progressively dealuminates the framework, thereby irreversibly deactivating the catalyst. It has also been theorized that the water combines with the aluminum present and adversely affects the catalytically active sites of such catalysts.

Oxides of carbon and sulfur-containing compounds are also catalytic poisons. It is believed that these poisons occupy the acidic sites where the majority of catalytic activity occurs. Although not wishing to be bound by theory, it is believed that the silicalite catalyst of the present invention resist poisoning by these contaminants.

In addition to the physical distinctions between the crystalline silica polymorph silicalite type catalyst and the more conventional aluminosilicate zeolites, several functional distinctions are also apparent in regard to the use of these catalysts as olefinic conversion catalysts. For example, ZSM type aluminosilicate zeolites reportedly rapidly lose their catalytic activity in the presence of even minor amounts of water. The crystalline silica polymorph silicalite materials of the present invention are useful as olefinic conversion catalysts even in the presence of water and/or steam. In addition, the catalysts useful in the present invention are unmodified in that no special chemical, thermal or steam pretreatment of the catalysts as synthesized is necessary prior to their use in the described process.

The process of the present invention can be carried out using a variety of process equipment including a reactor vessel having a hydrocarbon conversion zone which contains the silicalite catalyst material. Either single or multiple catalysts beds can be employed in the reaction zone utilizing a fixed bed, moving bed or fluidized bed. Reactants can be admixed and preheated prior to introduction into the reaction zone where they contact catalyst beds under conversion conditions further specified below. After a controlled residence time within the reaction zone, the converted hydrocarbon charge passes out of the reactor where the desired products are collected by cooling or other standard recovery or separation techniques. In a preferred embodiment, the silicalite catalyst employed by the subject invention is utilized to convert a refinery stream containing an olefinic mixture contaminated with either sulfur containing compounds oxides of carbon, or water or mixtures thereof. These refinery streams can most typically be found in the off-gas of any unit which produces olefins in the refinery such as a fluidized catalytic cracker, a moving bed catalytic cracker, a visbreaker, coker or a Dubbs unit. In the process of the present invention, the refinery off-gas feed material may be routed directly to the olefin conversion reactor without the need for pretreatment to remove the sulfur containing compounds, oxides of carbon or water. It should be realized, however, that a certain amount of water will be removed from the refinery off-gas by normal refinery separation equipment such as the primary or secondary sponge absorber. The olefins most prevalent in these off-gas streams are ethylene and propylene. The present invention, however, encompasses other olefins such as butylene.

In a preferred embodiment, the olefinic feedstock is converted to higher molecular weight hydrocarbons in the presence of the silicalite catalyst material under conversion conditions. Conversion inlet temperatures should range between about 350° C. to about 650° C.; however temperatures between about 380° C. and about 520° C. are preferred. Pressures in the range from about 30 psig to about 300 psig are utilized. Preferred pressures are from about 100 to about 200 psig.

Generally, the rate of introduction of feed material is at a weight hourly space velocity based upon the weight of total feed per weight of catalyst per hour from about 5 to about 50. The preferred weight hourly space velocity is from about 10 to about 20.

When employing the present process to produce gasoline range products from olefins, the preferred silicalite catalysts are those having a crystallite size from about 1 micron to about 5 microns. It has been found that the smaller crystallite sizes are more catalytically active. The catalyst material employed by the process of the subject invention is a true crystalline silica material as opposed to a zeolitic material which by definition, is a silicate of aluminum and either sodium or calcium, or both, which demonstrates ion exchange capacity. The crystalline silica materials used as catalysts in the present invention are silica polymorphs whose structures have been designated as "silicalite". These materials, in contrast to aluminosilicate zeolites, demonstrate no appreciable ion exchange properties. Aluminum may be present in these silicalite catalyst materials as a result of impurities in the silica source used to prepare the catalyst, but silicalite containing such aluminum or other oxide impurities can in no sense be considered a metallosilicate since $AlO_4^-$ tetrahedra do not comprise a portion of the crystalline silica framework.

Further description methods for preparing the silicalite catalysts used in the process of the present invention are set forth in U.S. Pat. No. 4,061,724 by Grose, which is incorporated in its entirety herein by reference.

The process of the present invention can be further illustrated through the following examples which are intended to be illustrative rather than limitative of the present invention.

EXAMPLE 1

A pilot plant having a fixed bed reactor was utilized. A sample of off-gas from a refinery fluidized catalytic cracker (FCC) was collected from the discharge side of the secondary sponge absorber. In some cases as noted, the hydrogen sulfide in the stream was removed. The contents of the FCC off-gas stream based upon the mole % of the total feed material were as follows:

|  | Runs 1 and 2 | Runs 3–7 | Runs 8 |
|---|---|---|---|
| $N_2$ | 11.4 | 12.8 | 13.2 |
| $H_2$ | 10.6 | 16.1 | 14.9 |
| $C_1$ | 21.3 | 25.1 | 23.3 |
| $C_2$ | 11.3 | 13.5 | 12.5 |
| $C_2^=$ | 10.9 | 12.6 | 11.7 |
| $C_3$ | 9.7 | 5.4 | 3.4 |
| $C_3^=$ | 10.4 | 9 | 8 |
| $C_4$ | 1.3 | 1.1 | 1.0 |
| $C_4^=$ | 0.8 | 0.9 | 0.9 |
| iso-$C_5$ | 0.1 | 0.1 | 0.1 |
| n-$C_5$ | 0.1 | — | — |
| $C_5+$ | 0.5 | 0.2 | 0.6 |
| $CO_2$ | 1.8 | 0.4 | 1.9 |
| CO | 2.1 | 2.5 | 2.2 |
| $H_2S$ | 7.4 | — | 6.3 |

The off-gas products were introduced into a reactor and brought up to temperature before reaching the reaction zone which contained a bed of silicalite catalyst material, having a particle size of 20–40 mesh, and a bed depth of approximately 10 centimeters. The reactor was a concentric cylinder 48 inches in length with a ½ inch pipe outer wall and ¼ inch tubing thermowall. In some cases, water was injected into the reactor along with the off-gas feed. A high pressure liquid-gas separator was used to collect the liquid product.

Eight runs were performed and the product stream from the reaction zone was analyzed by gas chromotography to obtain the product makeup by weight based upon the total weight of the feed material entering the reactor. The results were as shown on Table I. Averages in Table I were based upon five sample runs unless otherwise noted. Liquid products included non-aromatics, benzene, toluene, ethylbenzene, xylene and $C_9+$. The average conversion of olefins to higher molecular weight hydrocarbons based upon the weight of olefins in the feed was greater than 40%.

TABLE I

| Run | Avg. Inlet Temp/Pres. °C./psig | Steam | $H_2S$ | Avg. WHSV | Average Yield of Isolated Liquid Product (wt. % of feed) | Average Aromatics Content of Isolated Liquids (wt. % of Liquid Product) | Av. Total Yield incl. $C_4^=$ (wt. % of feed) (4) | Av. Total Yield w/o $C_4^=$ (wt. % of feed) (4) | Av. Total Yield w/o $C_4^=$ (3) (4) |
|---|---|---|---|---|---|---|---|---|---|
| 1 | 346/80 | None | Not removed | 52 (c) 14 (b) | 3.09 (5) | 10.44 | 13.58 | 10.76 | 34.51 |
| 4 | 446/80 | None | Removed | 42 (a) 10 (d) (1) | 3.74 | 34.67 | 16.17 | 12.36 | 35.87 |
| 8 | 412/155 | None | Not Removed | 12 | 5.54 | 59.83 | 20.71 | 17.18 | 55.0 |
| 3 | 414 (d) 454 (c) (2) | None | Removed | 10 | 6.63 | 68.92 | 15.37 | 14.08 | 40.88 |
| 6 | 400/90 | None | Removed | 14 | 3.67 | 58.78 | 21.93 | 18.19 | 52.81 |
| 7 | 396/85 | 0.4 ml/min | Removed | 14 | 1.91 | 53.81 | 18.55 | 14.57 | 42.30 |
| 5 | 450/102 | 0.4 ml/min | Removed | 12 | 3.52 | 70.20 | 15.48 | 12.23 | 35.50 |

(a) 1 sample
(b) 2 samples
(c) 3 samples
(d) 4 samples
(1) Conversion of $C_2^=$ and $C_3^=$ increased when WHSV lowered.
(2) Conversion of $C_2^=$ and $C_3^=$ decreased when temperature increased.
(3) Yields in weight % based on the amount of olefins in the feed.
(4) Includes the $C_5^+$ components found in the gas. These were assumed to have a Mol. wt of 78.
(5) Liquid of one sample contained 1.5 wt. % sulfur.

Water was added as co-feed in the process of the present invention because water, when converted to steam inside the reactor, has been found to slow deactivation of the silicalite catalyst. The amount of water added was significantly higher than would be found in a fully saturated olefinic feed mixture at reactor inlet pressure and temperature.

Although several specific embodiments of the present invention have been described in the detailed description above and in the examples, this description is not intended to limit the invention to the particular form or embodiments disclosed herein since they are to be recognized as illustrative rather than limitative, and it will be obvious to those skilled in the art that the invention is not so limited. Thus, the invention is declared to cover all changes and modifications of the specific examples of the invention herein disclosed for purposes of illustration which do not constitute departure from the spirit and scope of the invention.

The embodiments of the invention in which an exclusive property or privilege is claimed is defined as follows:

1. A process for converting a gaseous olefinic feedstream containing a contaminant comprising a sulfur containing compound into hydrocarbons of higher molecular weight comprising passing the feed material under conversion conditions through a reaction zone containing an unmodified crystalline silica polymorph silicate catalyst.

2. The process of claim 1 wherein the hydrocarbons of higher molecular weight are gasoline range hydrocarbons.

3. The process of claim 1 wherein the catalytic poison is a mixture of sulfur containing compounds, oxides of carbon, and water.

4. The process of claim 1 wherein the majority of the olefins are selected from the group consisting of ethylene, propylene or mixtures thereof.

5. The process of claim 1 wherein the sulfur-containing compound is hydrogen sulfide.

6. The process of claim 1 wherein the conversion conditions comprise
   (a) temperatures in the range of about 350° C. to about 650° C.,
   (b) pressures in the range of about 30 psi to 300 psi, and
   (c) an olefinic content weight hourly space velocity from about 5 to about 50 based upon the weight of the feedstream.

7. The process of claim 1 wherein water is introduced into the reactor along with feedstream in an amount above that contained in the feedstream when fully saturated at reactor inlet pressure and ambient temperature.

8. The process of claim 1 wherein the feedstream comprises off-gas from a refinery catalytic cracking unit.

* * * * *